United States Patent [19]

Tachibana

[11] Patent Number: 5,197,946
[45] Date of Patent: Mar. 30, 1993

[54] INJECTION INSTRUMENT WITH ULTRASONIC OSCILLATING ELEMENT

[75] Inventor: Shunro Tachibana, 6-18, Kusagae 1-chome, Chuo-ku, Fukuoka-shi, Fukuoka-ken, Japan

[73] Assignees: Shunro Tachibana, Fukuoka; Sumitomo Electric Industries, Ltd., Osaka, both of Japan

[21] Appl. No.: 727,777

[22] Filed: Jul. 10, 1991

Related U.S. Application Data

[63] Continuation-in-part of Ser. No. 544,309, Jun. 27, 1990, abandoned.

[51] Int. Cl.⁵ ............................................. A61M 5/14
[52] U.S. Cl. ............................................. 604/22; 604/43
[58] Field of Search .................... 604/19, 21, 22, 35, 604/43; 128/24 AA, 200.16, 207.14

[56] References Cited

U.S. PATENT DOCUMENTS

| | | | |
|---|---|---|---|
| 3,430,625 | 3/1969 | McLeod, Jr. | 128/24 AA |
| 3,941,122 | 3/1976 | Jones | 128/24 AA |
| 4,425,115 | 1/1984 | Wuchinich | 604/22 |
| 4,601,698 | 7/1986 | Moulding, Jr. | 604/22 |
| 4,698,058 | 10/1987 | Greenfeld et al. | 604/22 |
| 4,808,153 | 1/1989 | Parisi | 604/22 |
| 4,936,281 | 6/1990 | Stasz | 604/22 |

FOREIGN PATENT DOCUMENTS 1066597 1/1984 U.S.S.R. ..................... 604/22

*Primary Examiner*—Edgar S. Burr
*Assistant Examiner*—Stephen R. Funk
*Attorney, Agent, or Firm*—Jordan and Hamburg

[57] ABSTRACT

A medicinal injection instrument for injecting a medicinal medium into a living body includes a tubular arrangement for conducting a medicinal medium to an injection site, the tubular arrangement having a distal end. An ultrasonic oscillator device has an ultrasonic oscillator element juxtaposed to the distal end such that when the instrument is inserted into a living body with the distal end disposed juxtaposed to the injection site, the ultrasonic oscillator element is also disposed juxtaposed to the injection site to thereby enhance diffusion and penetration of the medicinal medium into the body tissue.

4 Claims, 3 Drawing Sheets

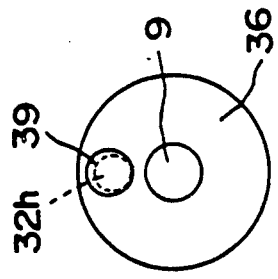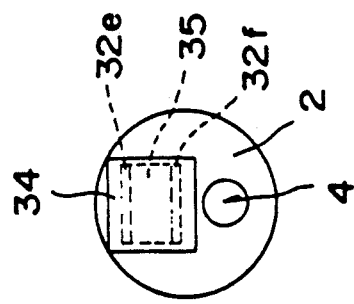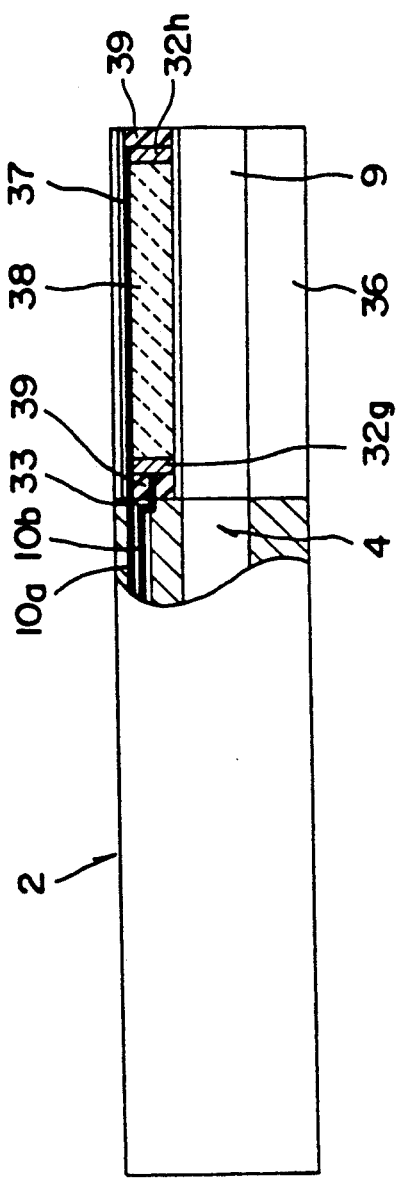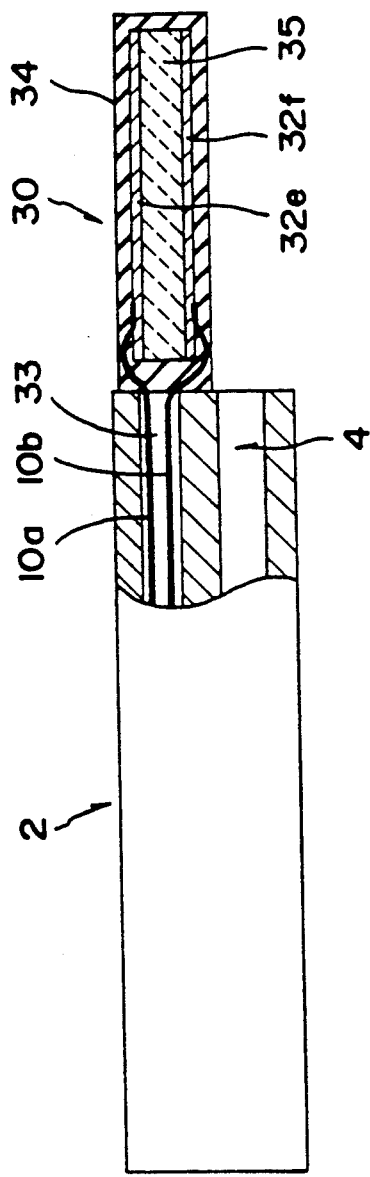

INJECTION INSTRUMENT WITH ULTRASONIC OSCILLATING ELEMENT

This is a continuation-in-part application of U.S. Ser. No. 07/544,309, filed Jun. 27, 1990, now abandoned.

BACKGROUND OF THE INVENTION

1. Field of the Invention

The present invention relates to an injection instrument for injecting medicinal fluid or the like into the human body through a catheter or other tubular injection instrument under the action of ultrasonic vibration at the injection site for improving diffusion and penetration of the injected medicinal fluid or the like. It is noted that in this specification, the term "injection" means injection of medicinal fluid or the like, unless otherwise specified.

2. Prior Art

Therapy for and prophylaxis against human disease generally comprises both oral and parenteral administration by means of injections, oral applications, suppositories, percutaneous applications, and other means. Particularly, methods for injecting directly into the body include local injection, intraarterial and intravenous injection, and in addition the method of injecting medicinal substance into target sites through an intravascular catheter, or the like.

With these methods of introducing medicinal substances directly into the body, there are some difficulties with diffusing and penetrating into the body tissues. As a countermeasure against this, chemical methods have mainly been used.

With special regard to the utilization of ultrasonic waves for improved diffusion and penetration of medicinal fluid administered through a catheter, the present inventor invented a vascular system cleaning instrument designed to transmit ultrasonic vibration generated at its proximal part which is attached to a catheter (Japanese Unexamined Patent Publication (KOKAI) No. 52071/1981).

The prior art technique of utilizing ultrasonic waves for improved diffusion and penetration of medicinal fluid administered, for example, through a catheter into the vascular system, especially to the retained substance therein, has difficulty in exhibiting a sufficient effect due to the damping of ultrasonic energy in the course of transmission. This is because the ultrasonic oscillating element is located outside the human body and far from the distal end of the catheter.

SUMMARY OF THE INVENTION

The inventor made further study on the technique of utilizing ultrasonic waves for improved diffusion and penetration of medicinal fluid or the like into the vascular system, and found that an oscillating element placed at the distal end of the catheter portion inserted in the body, and an ultrasonic oscillator at the proximal portion located outside of the body, both being electrically interconnected, remarkably improves the diffusion and penetration in the area of injection. This result has been obtained not only for catheters but also for other instruments inserted into the body. Thus, the present invention encompasses a wide range of injection instruments.

In short, this invention provides for injection instruments with an ultrasonic oscillating element having a proximal tubular part characterized by means for introducing medicinal fluid or the like and an ultrasonic oscillator or a connector which is electrically connected to an ultrasonic oscillating element located at the distal tubular part of the injection instrument.

BRIEF DESCRIPTION OF THE DRAWINGS

FIGS. 4A to 7A show fragmented and enlarged cross-sectional views of the distal end of injection instruments of Examples 4 to 7; and FIGS. 4B to 7B show front views of the distal end of injection instruments of Examples 4 to 7.

DESCRIPTION OF THE PREFERRED EMBODIMENTS

Injection instruments according to the invention as a rule have a construction comprising a proximal tubular part, with a central channel and an opening for introducing medicinal fluid or the like, and a distal tubular part consisting of a thin tube made of such material as metal, rubber, or plastic. A central channel connects the proximal tubular part with the distal tubular part. Such injection instruments can be used generally for the stomach, intestines, esophagus, trachea, vascular system, etc., and additionally for the injection of medicinal fluid directly into the body tissues.

Suitable oscillating elements for use in the invention include ceramic oscillating elements in the form of a column or centrally-bored cylinder having a diameter of about 1 to 10 mm, substantially the same as that of the distal tubular part, and flexible type oscillating film elements formed in a similar shape.

Oscillating elements having a central bore are utilized as passages through which medicinal fluid or the like is injected, or body fluid is drained. In the latter case, a cylindrical partition should be provided in both the proximal and distal tubular parts, to create two sections, consisting of a central channel for draining and a peripheral channel for injecting. Channels of one tubular part are aligned with the corresponding channels of the other tubular part. Also, an opening for allowing medicinal fluid or the like to flow out in the proximity of the oscillating element is provided.

With cylindrical oscillating elements without a central bore, the distal tubular body must be provided with an opening through which medicinal fluid or the like flows out at a location proximal to the oscillating element.

The ultrasonic oscillating element at the distal end is connected by conductive wires to an ultrasonic oscillator when the latter is attached to the proximal tubular part, or a connector connected to the ultrasonic oscillator when not attached thereto. The conductive wires may be embedded in the distal tubular part material or adhered to the inner surface thereof.

The above-described construction of the present invention permits medicinal fluid or the like to be injected under the action of vibration of the ultrasonic oscillating element which is located as near as possible to the target site of injection. The injected fluid therefore can be thoroughly diffused and penetrated into the tissues of the target site. Control of the power and amplitude of the ultrasonic wave associated with the oscillating element can be had as desired by means of the ultrasonic oscillator (whether o not attached to the injection instrument) connected to the oscillating element. This control permits fine adjustment appropriate to the injection site.

EXAMPLE 1

Figure 1:
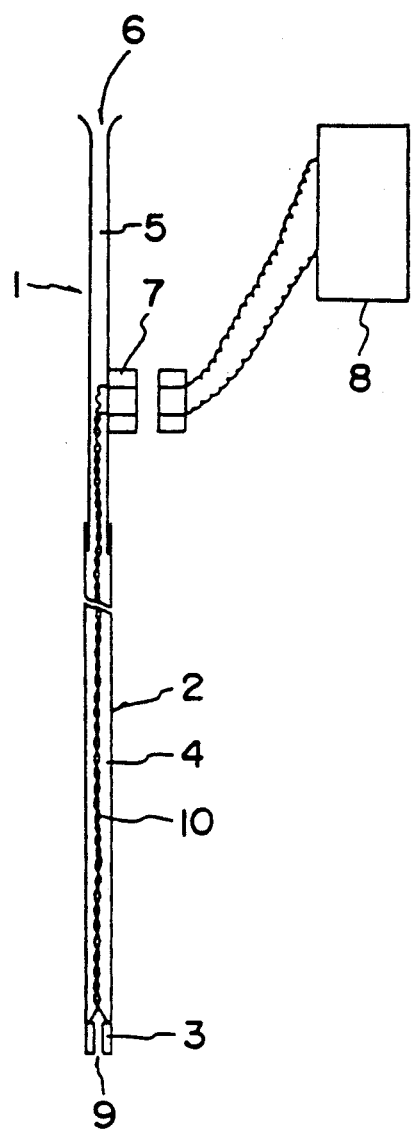
FIG. 1 is a sectional view of an injection instrument, Example 1, embodying the present invention.

As shown in FIG. 1, the proximal tubular part 1 of an injection instrument has an opening 6 at the proximal end thereof and a center channel 5 extending throughout the length thereof from the opening or inlet 6, through which injected fluids pass. To this tubular part is attached a connector 7 which is connected to an ultrasonic oscillator 8. The injection instrument is joined at the distal end thereof with a plastic, distal tubular part 2 forming a passage 4 for the injection of fluids, which part has a diameter of 1 to 10 mm. The distal tubular part 2 is provided at the distal end thereof (the opposite end to the inlet 6) with a cylindrical ceramic oscillating element 3 having an appropriate diameter for fitting into the distal tubular part 2 and a height of 1 to 10 mm. This cylindrical ceramic oscillating element 3 is provided with a central bore 9 of 0.5 to 9 mm in diameter.

The ceramic oscillating element 3 and the connector 7 are connected by conductive wires 10 which are located on or in the wall of the distal tubular part 2.

The connector 7 is connected to the ultrasonic oscillator 8.

EXAMPLE 2

This Example is distinguishable from Example 1 in that it has an oscillating element 3 without a bore.

It is the same as Example 1 except for the oscillating element 3 and the distal end portion of the distal tubular part 2.

Figure 2:
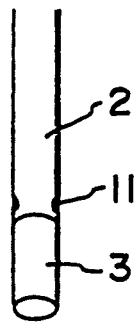
FIG. 2 is a fragmentary perspective view of Example 2, which illustrates the proximity of the joint between the distal tubular part and the ultrasonic oscillating element.

FIG. 2 shows the oscillating element 3 and the distal end portion of the distal tubular part 2.

As illustrated in FIG. 2, the ceramic oscillating element 3 has no bore. Instead, openings 11 are located slightly proximal to the joint between the distal end and the ceramic oscillating element 3.

EXAMPLE 3

Figure 3:
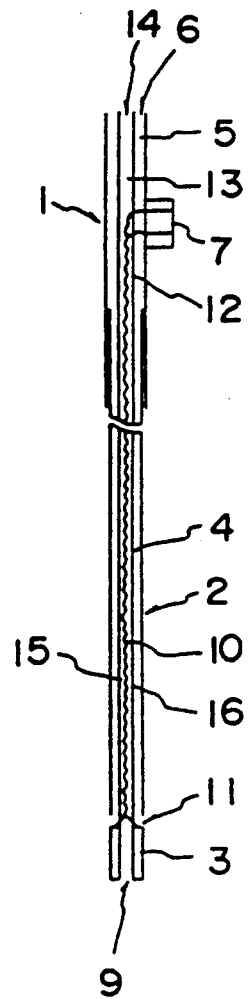
FIG. 3 is a sectional view of the injection instrument as per Example 3.

As shown in FIG. 3, the proximal tubular part 1 is separated by an internal tubular partition 12 into a center channel 13, having an outlet 14, for the drainage of body fluid and the peripheral channel 5, having an inlet 6, for the injection of medicinal fluid. To the proximal tubular part 1 is attached a connector 7 connected to an ultrasonic oscillator 8. Likewise, the distal tubular part 2 is provided with an internal tubular partition 16 for the separation of a central channel 15 for the drainage of body fluid and a peripheral channel 4 for the injection of medicinal fluid. The central and peripheral channels 13, 5 of the proximal tubular part 1 are joined to the corresponding central and peripheral channels 15, 4 of the distal tubular part 2, respectively.

A cylindrical ceramic oscillating element 3 with a central bore is located at the distal end of the distal tubular part 2. The bore and periphery of the oscillating element 3 are joined in alignment with the central channel 15 for the drainage of body fluid and the periphery of the distal tubular part 2, respectively. Openings 11 are provided, through which medicinal fluid or the like flow out of the wall of the distal tubular part 2 and at a location slightly proximal to the joint between the distal tubular part and the ceramic oscillating element 3.

The ceramic oscillating element 3 and the connector 7 are interconnected by conductive wires 10 which are adhered to the inner wall of the distal tubular part 2.

A connector 7 is connected to the ultrasonic oscillator 8.

Although the oscillating element 3 is connected to the ultrasonic oscillator 8 via the connector 7 in the above examples, it is possible to attach the ultrasonic oscillator 8 directly to the proximal tubular part 1, and connect the oscillating element 3 and the ultrasonic oscillator 8 with conductive wire 10 without a connector 7.

Furthermore, a thin metal plate mounted with a piezoelectric effect element such as a bimorph cell may be used instead of a cylindrical or column-shaped oscillating element 3.

FIGS. 4 to 7 show fragmented and enlarged views of the distal end of injection instruments of further Examples 4 to 7.

EXAMPLE 4

This Example shows a construction of the distal end of the injection instruments in detail.

Figure 4B:
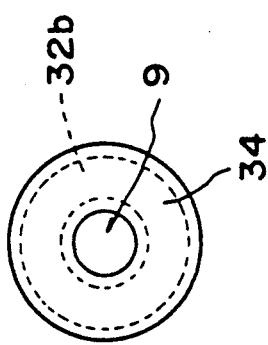
Figure 4A:
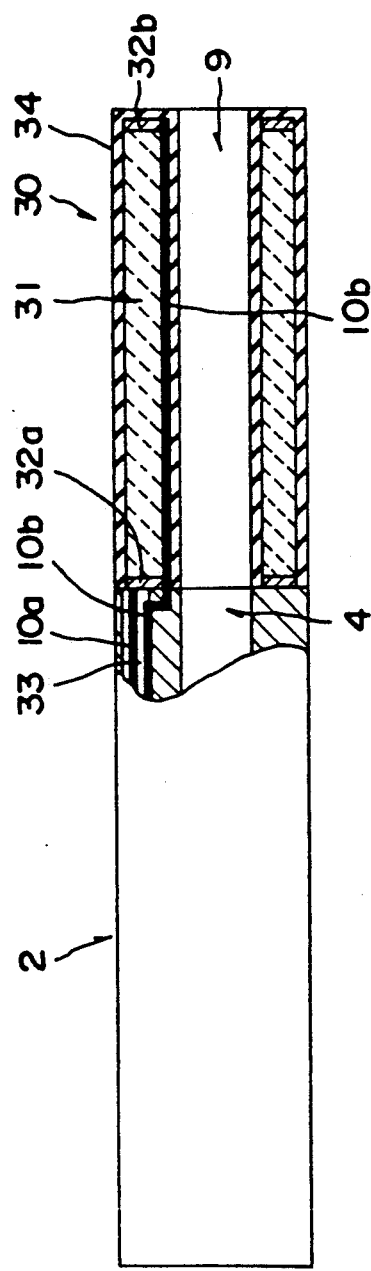
Figure 5B:
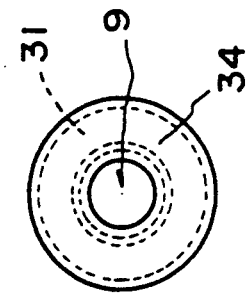
Figure 5A:
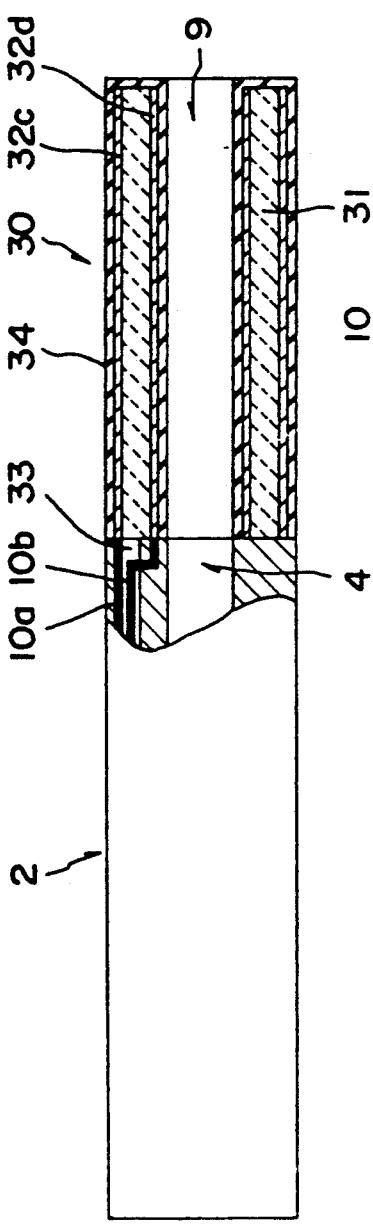

As shown in FIGS. 4A and 4B, a distal end of distal tubular part 2 is provided with a cylindrical oscillating element 31 such as a piezo electric element. This cylindrical oscillating element 31 is provided with a central bore 9 connected to a passage 4 of the distal tubular part 2. Ring-shaped electrodes 32a and 32b are attached to both end faces of the cylindrical oscillating element 31 and conductive wires 10a and 10b are connected respectively thereto. These conductive wires 10a, 10b have insulating coating and are lead through a conduit 33 to a proximal tubular part (not shown in FIG. 4A, refer to FIG. 1).

The inner and outer surface of the cylindrical oscillating element 31, a part of the conductive wire 10b, and the outer surface of electrode 32b are coated with an insulating resin layer 34 which may be formed by a molding method. Thus, electrode 32b is electrically isolated from any organ into which the injection instruments would be inserted, thereby preventing current leaks from flowing into the organ which may cause a side effect to the organ and a loss of driving energy.

The cylindrical oscillating element 31 itself, electrodes 32a and 32b, and the insulating resin layer 34 will be, hereafter collectively referred to as an ultrasonic oscillating element 30. In some cases, a part of the conductive wires 10a, 10b may be included in the ultrasonic oscillating element 30.

The ultrasonic oscillating element 30 has an appropriate inner and outer diameter for fitting into the distal tubular part 2, and the proximal side of the ultrasonic oscillating element 30 is fixed to the distal end of the distal tubular part 2 with appropriate means such as an adhesive agent.

In accordance with the injection instrument of Example 4, since the ring-shaped electrodes 32a, 32b are attached to both end faces of the cylindrical oscillating element 31, the driving signal from an ultrasonic oscillator (not shown in FIG. 4A, refer to FIG. 1) is applied along the axis of the cylindrical oscillating element 31. Therefore, ultrasonic vibration occurs along the axis of cylindrical oscillating element 31.

EXAMPLE 5

This Example is distinguishable from Example 4 in that cylindrical electrodes 32c and 32d are attached to the outer and inner surfaces of the cylindrical oscillating element 31.

In this Example, the outer surface of the outer cylindrical electrodes 32c, the inner surface of the inner cylindrical electrodes 32d, and the distal end face of the cylindrical oscillating element 31 are coated with an insulating resin layer 34.

In accordance with the injection instrument of Example 5, the driving signal is applied across the radial direction of the cylindrical oscillating element 31. Therefore, ultrasonic vibration travels in a radial direction from the cylindrical oscillating element 31, that is, ultrasonic vibration occurs concentrically.

EXAMPLE 6

This Example shows a construction of the distal end of the injection instruments in detail, in which the ultrasonic oscillating element of a rectangular plate type is used.

As shown in FIG. 6, rectangular plate type oscillating element 35 is sandwiched by a pair of rectangular electrodes 32e and 32f, with a pair of conductive wires 10a, 10b connected to the pair of rectangular electrodes 32e, 32f, respectively. The outer sides of both rectangular electrodes 32e, 32f, and four side faces of said rectangular plate type oscillating element 35 are coated with an insulating resin layer 34, thereby forming an ultrasonic oscillating element 30.

In accordance with the injection instrument of Example 6, the driving signal is applied across opposite planes of the rectangular plate type oscillating element 35. Therefore, ultrasonic vibration travels in a perpendicular direction to the plane of the rectangular plate type oscillating element 35.

EXAMPLE 7

This Example shows a construction of the distal end of the injection instruments in detail, in which the ultrasonic oscillating element of a rod type is used.

As shown in FIG. 7, there is a cylindrical insulating member 36 having a central bore 9 fitted into the passage 4 of the distal tubular part 2, and a penetrating hole 37 in which a rod type oscillating element 38 is disposed. The cylindrical insulating member 36 is made from synthetic resin, and the central bore 9 and penetrating hole 37 may be formed by a resin molding method. A pair of disc-like electrodes 32g and 32h are attached to both end faces of the rod type oscillating element 38 and conductive wires 10a and 10b are respectively connected thereto. In the construction process, the rod type oscillating element 38 with electrodes 32g, 32h, each connected to conductive wires 10a, 10b, is inserted into the penetrating hole 37, and both end openings of the penetrating hole 37 are sealed with insulating material 39.

According to the present invention, an ultrasonic oscillating element is disposed at the most distal end of the distal tubular part, therefore enabling ultrasonic vibration from the ultrasonic oscillating element to be applied to a target directly, and thereby improving the diffusion and penetration characteristics of the medicinal fluid. In this Specification, an ultrasonic oscillating element means not only the oscillating element itself, but includes the electrodes attached to the oscillating element, an insulating resin layer, conductive wires, and other parts that integrally function with the oscillating element.

A porous oscillating element may be used instead of a cylindrical oscillating element 3, the former having a central bore and injecting medicinal fluid through pores.

According to the invention, the above-described instruments are useful not only for the injection of medicinal fluid or the like but also for the drainage of fluids from the organ(s) accompanied by the breaking-up and dissolution of aggregates by the action of ultrasonic waves.

The present invention is unique in its ability to carry out the injection of fluids into tissues with remarkably improved diffusion and penetration. For example, the treatment of coronary thrombosis, wherein an injection instrument according to the invention is inserted into the proximity of thrombus or thrombi and then a thrombolytic agent such as urokinase is injected, can result in markedly higher thrombolysis, shortened time taken for causing the bloodstream to recur, and improved hematological findings.

An injection instrument, especially as in Example 3 of the present invention, can be used for the treatment of hematoma-form cerebral hemorrhage in procedures including insertion into the hematoma and the injection of a thrombolytic agent, in combination with ultrasonic radiation, with the result of causing the hematoma to dissolve and withdraw through the tubular parts. This enables remarkably-widened uses of injection instruments for the treatment of cerebral hemorrhages.

Although the present invention has been fully described by way of example with reference to the accompanying drawings, it is to be understood that various changes and modifications will be apparent t those skilled in the art. Therefore, unless otherwise such changes and modifications depart from the scope of the invention, they should be construed as being included therein.

What is claimed is:

1. A medicinal injection instrument for injecting a medicinal medium into body tissue of a living body comprising a tubular means for conducting a medicinal medium to an injection site, said tubular means having a distal end portion, said distal end portion having a terminating end, an ultrasonic means comprising an ultrasonic oscillator element means disposed at said distal end portion and extending to said terminating end such that when the instrument is inserted into a living body with said distal end portion disposed juxtaposed to an injection site, said ultrasonic oscillator element means is also disposed juxtaposed to the injection site to thereby enhance diffusion and penetration of said medicinal medium into body tissue of said living body, said ultrasonic oscillating element means comprising a hollow cylindrical oscillating member having inner and outer cylindrical walls and cylindrical electrodes disposed on said inner and outer cylindrical walls.

2. A medicinal injection instrument for injecting a medicinal medium into body tissue of a living body comprising a tubular means for conducting a medicinal medium to an injection site, said tubular means having a distal end portion, said distal end portion having a terminating end, an ultrasonic means comprising an ultrasonic oscillator element means disposed at said distal end portion and extending to said terminating end such that when the instrument is inserted into a living body with said distal end portion disposed juxtaposed to an injection site, said ultrasonic oscillator element means is also disposed juxtaposed to the injection site to thereby enhance diffusion and penetration of said medicinal medium into body tissue of said living body, said ultrasonic oscillating element means comprising an oscillating plate member disposed between two flat electrodes, said oscillating plate member and said two flat electrodes each have a rectangular configuration.

3. A medicinal injection instrument for injecting a medicinal medium into body tissue of a living body comprising a tubular means for conducting a medicinal medium to an injection site, said tubular means having a distal end portion, said distal end portion having a terminating end, an ultrasonic means comprising an ultrasonic oscillator element means disposed at said distal end portion and extending to said terminating end such that when the instrument is inserted into a living body with said distal end portion disposed juxtaposed to an injection site, said ultrasonic oscillator element means is also disposed juxtaposed to the injection site to thereby enhance diffusion and penetration of said medicinal medium into body tissue of said living body, said ultrasonic oscillating element means comprising a hollow cylindrical insulating member having a central bore and a longitudinally extending passage spaced from said central bore, said ultrasonic oscillating element means further comprising an oscillating member disposed in said passage, said oscillating member having longitudinal ends, said ultrasonic oscillating means further comprising electrodes at said longitudinal ends of said oscillating member.

4. A medicinal injection instrument according to claim 3, wherein said ultrasonic oscillating element means further comprises insulating means sealing the longitudinal ends of said passage such that said oscillating member and said electrodes are sealed in said passage.

* * * * *